United States Patent [19]

Bull

[11] 4,259,349

[45] Mar. 31, 1981

[54] HALOBENZYL ESTER PESTICIDES

[75] Inventor: Michael J. Bull, Lower Halstow, England

[73] Assignee: Shell Oil Company, Houston, Tex.

[21] Appl. No.: 82,242

[22] Filed: Oct. 5, 1979

Related U.S. Application Data

[63] Continuation-in-part of Ser. No. 52,158, Jun. 26, 1979, abandoned.

[30] Foreign Application Priority Data

Oct. 13, 1978 [GB] United Kingdom ............... 40420/78
Sep. 17, 1979 [GB] United Kingdom ............... 32152/79

[51] Int. Cl.³ .................... A01N 53/00; C07C 69/743; C07C 121/66
[52] U.S. Cl. ............................... 424/305; 260/465 D; 424/304; 560/124
[58] Field of Search .................. 260/465 D; 560/124; 424/304, 305

[56] References Cited

U.S. PATENT DOCUMENTS 3,567,740  3/1971  Matsui et al. .................. 260/347.4
3,792,079  2/1974  D'Orazio ........................ 560/124
4,183,950  1/1980  Naumann et al. ............... 424/305

FOREIGN PATENT DOCUMENTS 862109  6/1978  Belgium .
1437815  6/1976  United Kingdom .

*Primary Examiner*—Dolph H. Torrence

[57] ABSTRACT

Compounds of the formula

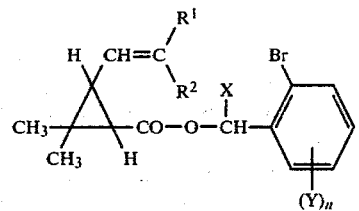

wherein $R^1$ is H or halogen, $R^2$ is halogen, X is H, cyano, ethynyl or thioamido, n is an integer from 1–4 and each Y is H or halogen, are useful as pesticides.

6 Claims, No Drawings

HALOBENZYL ESTER PESTICIDES

CROSS-REFERENCE TO RELATED APPLICATIONS

This application is a continuation-in-part of application Ser. No. 52,158, filed June 26, 1979 now abandoned.

BACKGROUND OF THE INVENTION

1. Field of the Invention

This invention relates to 2-halobenzyl esters, to their preparation, and to compositions containing them for use as pesticides, especially as insecticides and acaricides.

2. Description of the Prior Art

Belgian Patent Specification No. 862,109 relates to a general class of compounds of formula

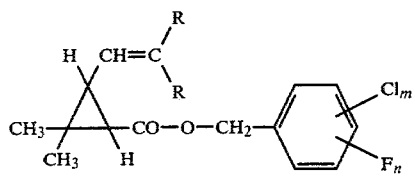

where the R moieties, which may be the same or different, are selected from fluoro, chloro and bromo, and when R is fluoro or bromo, m is 0 to 5 and n is 0 to 5 provided that m and n cannot both be 0; when R is chloro, m is 0 to 4 and n is 1 to 5; and when m is 0 and n is 5, R may be methyl in addition to the other moieties. This Belgian Patent also mentions generally the existence in the prior art of similar compounds in which the benzyl moiety is substituted exclusively with chlorine atoms.

SUMMARY OF THE INVENTION

The present invention is directed to 2-bromobenzyl esters of the formula I

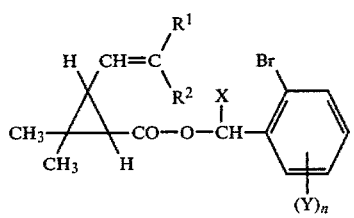

where $R^1$ is hydrogen, fluorine, chlorine, bromine or iodine, $R^2$ is fluorine, chlorine, bromine or iodine, X is hydrogen, cyano, ethynyl or thioamido, n is an integer from 1 to 4 and each Y is independently selected from hydrogen, fluorine, chlorine, bromine or iodine.

It should be noted that the compounds of formula I possess two or three centres of asymmetry, depending on the nature of the substitutent X. As will be appreciated by those skilled in the art, the compounds of formula I may exist as geometrical and optical isomers, mixtures of isomers and racemates.

Preferred compounds of formula I have one or more of the following features:
(i) $R^1$ and $R^2$ are independently selected from fluorine, chlorine and bromine,
(ii) X is hydrogen or cyano,
(iii) X is hydrogen,
(iv) n is 1,
(v) Y is selected from hydrogen, fluorine, chlorine or bromine,
(vi) Y is a 6-fluoro, 6-chloro or 6-bromo substituent,
(vii) the 2(2-$R^1$-2-$R^2$-vinyl)-3,3-dimethylcyclopropane carboxyl moiety has cis-configuration,
(viii) the 2(2-$R^1$-2-$R^2$-vinyl)-3,3-dimethylcyclopropane carboxyl moiety has 1R-cis-configuration.

The 2-bromobenzyl esters of formula I may be prepared by analogous methods to those used for known compounds. A convenient process comprises reaction of a compound of formula II:

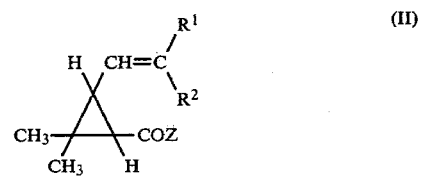

with a compound of formula III:

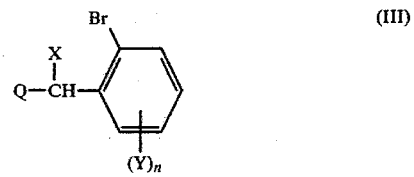

where $R^1$, $R^2$, X, Y and n are as defined above, one of Q and Z represents a halogen atom, preferably a chlorine or bromine atom, and and the other represents a hydroxy group. The reaction is preferably carried out in the presence of a suitable base, for example, a tertiary amine such as triethylamine or an alkali metal carbonate such as potassium or sodium carbonate, in the presence of an inert solvent. Conveniently Z represents a hydroxy group and Q represents a chlorine or bromine atom.

The compounds of formula II above and their individual isomers are conveniently prepared in known manner, for example as described in U.K. Patent Specifications Nos. 1,413,491 and 1,448,228.

The compounds of formula III above where X is hydrogen and Q is halogen are conveniently prepared by halogenation of corresponding halobromotoluenes. The halobromotoluenes are obtainable by introduction of the appropriate halogen via diazotisation of the appropriate halotoluidine. Halotoluidines may be prepared by reduction of the corresponding halonitrotoluene by known methods e.g. Entwistle et al, J.C.S. Perkin I, 1977 Pages 443 and 444. Compounds of formula III where X is hydrogen and Q is hydroxy may be prepared by hydrolysis of the compounds where Q is halogen.

Compounds of formula III where X is cyano, ethynyl or thioamido may be prepared in known manner from those where X is hydrogen via the corresponding aldehyde.

The 2-bromobenzyl esters according to the invention are of interest as pesticides especially as insecticides and acaricides for domestic and agricultural outlets. The invention therefore includes within its scope pesticidal compositions comprising a carrier and/or a surface-active agent together with, as active ingredient, a 2- bromobenzyl ester of formula I. The invention also includes a method of combating insect, tick and/or acarid pests at a locus which comprises applying to the locus a pesticidally effective amount of a 2-bromobenzyl ester of the invention or composition containing such a compound.

The term "carrier" as used herein means a material, which may be inorganic or organic and of synthetic or natural origin, with which the active compound is mixed or formulated to facilitate its application to the plant, seed, soil or other object to be treated, or its storage, transport or handling. The carrier may be a solid or a liquid. Any of the materials usually applied in formulating pesticides, herbicides, or fungicides may be used as the carrier.

Suitable solid carriers are natural and synthetic clays and silicates, for example natural silicas such as diatomacious earths; magnesium silicates, for example, talcs; magnesium aluminium silicates, for example attapulgites and vermiculites; aluminium silicates, for example, kaolinites, montmorillinites and micas; calcium carbonates; calcium sulphate; synthetic hydrated silicon oxides and synthetic calcium or aluminium silicates; elements for example, carbon and sulphur; natural and synthetic resins such as, for example coumarone resins, polyvinyl chloride and styrene polymers and copolymers; solid polychlorophenols; bitumen; waxes such as for example, beeswax, paraffin wax, and chlorinated mineral waxes; and solid fertilisers, for example superphosphates.

Suitable liquid carriers are water, alcohols, for example, isopropanol and glycols; ketones for example, acetone, methyl ethyl ketone, and cyclohexanone; ethers; aromatic hydrocarbons, for example, benzene, toluene and xylene; petroleum fractions, for example, kerosine and light mineral oils; chlorinated hydrocarbons, for example, carbon tetrachloride, perchloroethylene, trichloroethane; and liquefied normally vaporous, gaseous compounds. Mixtures of different liquids are often suitable.

The surface-active agent may be an emulsifying agent or a dispersing agent or a wetting agent; it may be non-ionic or ionic. Any of the surface-active agents usually applied in formulating pesticides herbicides or fungicides, may be used. Examples of suitable surface-active agents are the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols for example p-octylphenol or p-octylcresol, with ethylene oxide and/or propylene oxide; sulphates or sulphonates of these condensation products; alkali or alkaline earther metal salts, preferably sodium salts, or sulphuric or sulphonic acid esters containing at least 10 carbon atoms in the molecule, for example, sodium lauryl sulphate, sodium secondary alkyl sulphates, sodium salts of sulphonated castor oil, and sodium alkylaryl sulphonates such as sodium dodecylbenzene sulphate; and polymers of ethylene oxide and copolymers of ethylene oxide and propylene oxide.

The compositions of the invention may be formulated as wettable powders, dusts, granules, solutions, emulsifiable concentrates, emulsions, suspension concentrates and aerosols. Wettable powders are usually compounded to contain 25, 50 and 75% of toxicant and usually contain, in addition, to solid carrier, 3½–0% w of a dispersing agent and, where necessary, 0–10% w of stabiliser(s) and/or other additives such as penetrants or stickers. Dusts are usually formulated as a dust concentrate having a similar composition to that of a wettable powder but without a dispersant, and are diluted in the field with further solid carrier to give a composition usually containing ½–10% w of toxicant. Granules are usually prepared to have a size between 10 and 100 BS mesh (1.676–0.152 mm), and may be manufactured by agglomeration or impregnation techniques. Generally, granules will contain ½–25% w toxicant and 0–10% w of additives such as stabilisers, slow release modifiers and binding agents. Emulsifiable concentrates usually contain, in addition to the solvent and, when necessary, co-solvent, 10–50% w toxicant, 2–20% w/v emulsifiers and 0–20% w/v of appropriate additives such as stabilisers, penetrants and corrosion inhibitors. Suspension concentrates are compounded so as to obtain a stable, non-sedimenting flowable product and usually contain 10–75% w toxicant, 0.5–15% w of dispersing agents, 0.1–10% w of suspending agents such as protective colloids and thixotropic agents, 0–10% w of appropriate additives such as defoamers, corrosion inhibitors, stabilisers, penetrants and stickers, and as carrier, water or an organic liquid in which the toxicant is substantially insoluble; certain organic solids or inorganic salts may be dissolved in the carrier to assist in preventing sedimentation or as anti-freeze agents for water.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have a thick "mayonnaise"-like consistency.

The compositions of the invention may also contain other ingredients, for example, other compounds possessing pesticidal, herbicidal or fungicidal properties.

The invention will be better understood from the following Examples.

EXAMPLE 1—Preparation of 1:1 cis/trans 2-bromo-6-chlorobenzyl 2-(2,2-dichlorovinyl)-3,3-dimethylcyclopropane carboxylate (a) Preparation of 2-bromo-6-chlorobenzylbromide 2-bromo-6-chlorotoluene (20.55 g) and N-bromosuccinimide (19.6 g) were stirred together in carbon tetrachloride (100 ml) under reflux for 22 hours exposure to radiation from an infrared lamp. The resulting solution was cooled in ice, filtered and evaporated to yield the title product which was dissolved in petroleum ether (60–80). Part was recrystallised therefrom as pink needles (8.5 g) and part was recovered by evaporation as a dark orange solid (17.7 g) (total yield 26.2 g. 92%).

(b) Preparation of 1:1 cis/trans 2-bromo-6-chlorobenzyl 2-(2,2-dichlorovinyl)-3,3-dimethylcyclopropane carboxylate 1:1 cis/trans 2-(2,2-dichlorovinyl)-3,3-dimethylcyclopropane carboxylic acid (2.3 g), 2-bromo-6-chlorobenzylbromide (2.85 g) and potassium carbonate (1.6 g) were stirred together in acetone (30 ml) under reflux for 6 hours. The reaction mixture was cooled, diluted with water, and extracted three times with 50 ml portions of diethyl ether. The combined ether extracts were washed with water and with aqueous sodium bicarbonate solution (three times), dried over magnesium sulphate and evaporated to give the orange title product (4. g, 98%) m.p. 61°–67° C.

Analysis Calculated $C_{15}H_{15}BrCl_3O_2$: C, 43.6; H, 3.4; Br, 19.4; Cl, 25.9. Found: C, 43.8; H, 3.4; Br, 19.1; Cl, 25.4.

EXAMPLES 2 TO 11

By similar methods to that employed in Example 1, there were also prepared the following compounds:

1,R-cis-2-bromo-6-chlorobenzyl 2-(2,2-difluorovinyl)-3,3-dimethylcyclopropane carboxylate (yield 76%) $n_D^{19} = 1.533$, $[\alpha]_D^{25} = -15.45$ ($C_2CHCl_3$)

1:1 cis/trans-2-bromobenzyl 2-(2,2-dichlorovinyl)-3,3-dimethylcyclopropane carboxylate (yield 89%) $n_D^{23} = 1.5606$ cis-2-bromobenzyl 2-(2,2-dichlorovinyl)-3,3-dimethylcyclopropane carboxylate (yield 80%) $n_D^{23} = 1.5614$ trans-2-bromobenzyl 2-(2,2-dichlorovinyl)-3,3-dimethylcyclopropane carboxylate (yield 82%) $n_D^{23} = 1.5600$ 1,R-cis-2-bromo-6-chlorobenzyl 2(2,2-dichlorovinyl)-3,3-dimethylcyclopropane carboxylate (yield 90%) $n_D^{21} = 1.5682$ $[\alpha]_D^{25} = -26.8$ (C2 $CHCl_3$)

cis-2-bromo-6-chlorobenzyl 2(2,2-dibromovinyl)-3,3-dimethylcyclopropane carboxylate. (yield 84%) m.p. 101°–3° C.

cis-2-bromo-6-fluorobenzyl 2-(2-chloro-2-fluorovinyl)-3,3-dimethylcyclopropane carboxylate (yield 65%) m.p. 53°–54° C.

cis-2-bromo-6-fluorobenzyl 2-(2,2-dichlorovinyl)-3,3-dimethylcyclopropane carboxylate (yield 66%) m.p. 68°–69° C.

1,R-cis-2-bromo-6-fluorobenzyl 2-(2,2-dichlorovinyl)-3,3-dimethylcyclopropane carboxylate (yield 81%) $n_D^{21} = 1.551$, $[\alpha]_D^{25} = -21.9$ (C2 $CHCl_3$)

cis-2-bromo-6-fluorobenzyl 2-(2,2-dibromovinyl)-3,3-dimethylcyclopropane carboxylate (yield 74%) m.p. 66°–67° C.

Pesticidal Tests

The insecticidal and tickicidal activity of the compounds according to the present invention was assessed employing the following pests:

Insects:
*Musca domestica* (M.d.)
*Spodoptera littoralis* (S.l.)
*Aphis fabae* (A.f.)
*Heliothis zea* (H.z.)

Mites:
*Tetranychus urticae* (T.u.)

The test methods employed for each species appear below:

(i) *Musca domestica* (M.d.)

A 0.4% by weight solution in acetone of the compound to be tested was prepared and taken up in a micrometer syringe. Two to three day old adult female houseflies (*Musca domestica*) were anaesthetized with carbon dioxide, and 1 μl of the test solution was applied to the ventral side of the abdomen of each fly, 20 flies being tested. The treated flies were held in glass jars covered with paper tissue held by an elastic band. Cotton-wool pads soaked in dilute sugar solution were placed on top of the tissue as food. After 24 hours the percentage of dead and moribund flies were recorded.

(ii) *Spodoptera littoralis* (S.l.)

Pairs of leaves were removed from broad bean plants and placed on filter paper inside plastic petri dishes. The leaves were sprayed on the undersurface with an aqueous formulation containing 20% by weight of acetone, 0.05% by weight of TRITON X-100 (Trade Mark) as wetting agent and 0.4% by weight of the compound to be tested. Varying concentrations were obtained by diluting the formulation. After spraying the leaves were left to ½–1 hour drying period and then each leaf pair was infested with ten larvae of the Egyptian cotton leafworm (*Spodoptera littoralis*). After 24 hours the percentages of dead and moribund larvae were recorded.

(iii) *Aphis fabae* (A.f.)

Tests were carried out on adult aphids (*Aphis fabae*) by similar methods to that used for *Spodoptera littoralis* in (ii) above.

(iv) *Heliothis zea* (H.z.)

The compounds to be tested were incorporated in aqueous solutions containing 20% by weight of acetone, 0.04% by weight of Atlox 1045A (Trade Mark) and 0.2% by weight of the test compound, more dilute solutions for dosagemortality curves being made by diluting the 0.2% solution with an aqueous solution of 0.05% by weight of Atlox 1045A. Cut Windsor broad bean plants were placed on a turntable and sprayed with 4 ml of test solution. Immediately after spraying, 5 corn earworm larvae (*Heliothis zea*) were transferred to each plant which was inserted into water through a hole in a test board and the environment was maintained at a temperature of 27° C. and 40–50% relative humidity. Mortality was assessed after 44 to 46 hours.

(v) *Tetranychus urticae* (T.u.)

Discs were cut from the leaves of French bean plants and were placed on filter paper kept moist by a cotton-wool wick dipping into water. Each disc was infested with ten adult mites, and the discs were then sprayed with a solution or suspension of the test compound in acetonewater (20:80) containing 0.05% of TRITON X-100 (Trade Mark) as wetting agent. After 24 hours the percentage of dead and moribund mites was assessed.

(vi) *Boophilus microplus* (B.m.)

A 0.1% by weight solution of the compound to be tested was prepared in acetone containing 10% by weight of polyethylene glycol. Varying concentrations were obtained by diluting this solution. 1 ml of test solution was applied evenly to a filter paper inside a petri dish. When sufficiently dry, the filter paper was folded in half and crimped along part of its outer edge to form a packet. About 80–100 two of three week old one-host cattle tick larvae (*Boophilus microplus*) were transferred into the packet, which was then completed sealed. The packet was then placed in an incubator at 27° C. and 80% relative humidity. After 24 hours the packet was opened and the percentage of dead and moribund larvae was assessed.

The results are shown in Table I in which the test species are identified by the initials noted above and the activity of the compound is expressed in the form of its Toxicity Index (T.I.) which is calculated from the following equation:

$$\text{Toxicity Index } (T.I.) = \frac{LC_{50} \text{ of ethyl parathion (standard)}}{LC_{50} \text{ of test compound}}$$

The knockdown activity of the compounds according to the invention was assessed employing the common housefly (*Musca domestica*) by means of the Kearns-March chamber test.

The Kearns-March chamber consists of a 2 foot×1 foot transparent glass cylinder into which flies can be introduced through a sliding panel at one end. 0.2 ml of a 20% MeCl₂/80% Shellsol K solution containing active material was sprayed for 1½ seconds into the chamber at 10 psi and the air supply kept on for a further two seconds to facilitate even distribution of the spray. About 70 flies were used in each treatment and knockdown counts made at 1, 2, 3, 4, 5, 7 and 10 minutes after spraying. Compounds are graded into six classes according to the concentration of toxicant required to achieve 90% knockdown after ten minutes, that is to say Class 0 90% at 10 minutes=concentration 0.025%
Class 1 90% at 10 minutes=concentration 0.05%
Class 2 90% at 10 minutes=concentration 0.1%
Class 3 90% at 10 minutes=concentration 0.2%
Class 4 90% at 10 minutes=concentration 0.4%
Class 5 90% at 10 minutes=concentration 0.4%
Class 6 No knockdown at 0.4%

The results of these tests are also given in Table I.

TABLE I

| Compound of Example | Toxicity Index | | | | | | Knockdown Class |
|---|---|---|---|---|---|---|---|
| | M.d. | S.l. | A.f. | H.z. | T.u. | B.m. | |
| 1 | 40 | 140 | 27 | 46 | 10 | 422 | 2 |
| 2 | 25 | 134 | 33 | + | 7 | 1240 | 0 |
| 3 | 4.5 | 9 | 6 | 8.9 | 13 | 8 | 4 |
| 4 | 4.6 | 20 | 7 | 14 | 21 | 15 | 4 |
| 5 | 5.4 | 9 | 5 | 6.2 | 4 | + | 4 |
| 6 | 43 | 144 | 12 | 78 | 63 | 594 | 1 |
| 7 | 15 | 75 | 14 | 32 | + | 147 | 4 |
| 8 | 16 | 34 | 14 | + | 27 | 290 | 2 |
| 9 | 20 | 35 | 9 | + | 24 | 238 | 1 |
| 10 | 15 | 44 | 19 | + | 14 | 80 | 3 |
| 11 | 34 | 48 | 27 | + | 49 | 481 | 2 |

+ not yet tested

I claim:
1. A compound of the formula

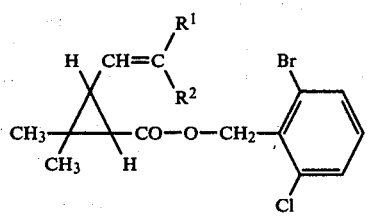

wherein $R^1$ and $R^2$ are both fluorine or chlorine, said compound having the cis/trans optical configuration or the cis optical configuration, substantially free of other optical isomers.

2. A compound according to claim 1 wherein $R^1$ and $R^2$ are fluorine.

3. A compound according to claim 1 wherein $R^1$ and $R^2$ are chlorine.

4. A compound according to claim 3 or 2 which has the 1R, cis optical configuration.

5. An insecticidal composition comprising an insecticidally effective amount of a compound according to claim 1 and at least one surface-active agent or carrier.

6. A method of contolling insect pests which comprises applying to the pests on their habitat an insecticidally effective amount of a compound according to claim 1.

* * * * *

Dedication 4,259,349.—*Michael J. Bull*, Lower Halstow, United Kingdom. HALOBENZYL ESTER PESTICIDES. Patent dated Mar. 21, 1981. Dedication filed Sept. 8, 1981, by the assignee, *Shell Oil Co.*

Hereby dedicates to the Public the entire remaining term of said patent.

[*Official Gazette December 22, 1981.*]